US00PP08572P

United States Patent [19]

Wain

[11] Patent Number: Plant 8,572

[45] Date of Patent: Feb. 1, 1994

[54] CHRYSANTHEMUM PLANT NAMED 'MAKE TIME'

[75] Inventor: Peter Wain, Hayling Island, United Kingdom

[73] Assignee: Cleangro, Ltd., Havant, England

[21] Appl. No.: 898,217

[22] Filed: Jun. 12, 1992

[51] Int. Cl.[5] ..... A01H 5/00

[52] U.S. Cl. ..... Plt./76

[58] Field of Search ..... Plt. 76, 80, 81, 82

*Primary Examiner*—Howard J. Locker

*Attorney, Agent, or Firm*—Arnold, White & Durkee

[57] ABSTRACT

Chrysanthemum Make Time is a new cultivar, distinguished by its lavender-rose ray floret color, spreading to upright branching habit and exceptional number of flowers per break. Make Time was selected from among progeny of a cross between female parent Pink Arola and male parent Cindy. The new cultivar is distinguishable from other Chrysanthemums and from both parents in its full, robust branching habit arising from a large number of blooms per break. Make Time has an exceptionally long shelf life giving it a commercial advantage over several other Chrysanthemums.

1 Drawing Sheet

BACKGROUND OF THE NEW PLANT

The new Chrysanthemum cultivar was selected as one flowering plant from among the progeny of a cross made by Peter Wain between the female parent Pink Arola (U.S. Plant Pat. No. 6,129) and the male parent Chrysanthemum Cindy (U.S. Plant Pat. No. 6,838). Make Time differs from either parent in having an unusually large number of flowers per break which give the plant a full, yet compact and robust appearance. Make Time florets are lighter in color than the florets of the female parent Pink Arola. Make Time flower buds typically open cleanly, giving a healthy, full appearance unlike that of the male parent Cindy. Although Make Time is similar in color to the Chrysanthemum Charm (U.S. Plant Pat. No. 5,502), the number of flowers per break typically average 40% higher over a smaller diameter capitulum when grown under the same conditions. Make Time therefore can be grown as a CBR/Spray (central bud removal) pot throughout the year, saving time and cost of disbudding.

The cross which produced Make Time was made as part of a controlled breeding program conducted in Havant, Hampshire, England. Selection of Make Time was based on its distinctive flat form and exceptional number of flowers per break which distinguished it from other Chrysanthemum cultivars and appeared to make the plant desirable for commercial greenhouse production.

Make Time is similar in capitulum form, type and branching habit to the cultivar Charm described in U.S. Plant Pat. No. 5,502. Charm is normally grown as a disbud pot and the diameter across the capitulum when grown this way is 9.7 cm. Make Time is normally grown as a CBR (central bud removal) pot and the diameter of the capitulum when grown this way is 5.4 cm. Make Time has an average of 8.4 flowers per break which is significantly more than Charm which has 6.2 flowers per break. The larger number of flowers per break in Make Time makes it possible to grow this plant as a CBR/Spray (center bud removal) pot throughout the year which saves time and cost of disbudding. The number of flowers per pot also makes the plant very full and robust in appearance. Make Time has a similar average number of breaks per pinch to Charm. Make Time takes approximately 6 days longer than charm to flower. Make Time is very similar in color to Charm. Make Time ships well and provides the customer with an excellent plant with exceptional shelf life (blooming time) of 4–6 weeks.

The first act of asexual reproduction of Make Time was accomplished when vegetative cuttings were taken in April 1989 in a controlled environment in Havant, England by the inventor.

Horticultural examination of controlled flowerings of successive plantings has shown that the unique combination of characteristics as herein disclosed for Make Time are firmly fixed and are retained through successive generations of asexual reproduction.

Make Time has not been observed under all possible environmental conditions. The phenotype may vary significantly with variations in the environment such as temperature, light intensity and day length.

The following traits have been repeatedly observed and are determined to be basic characteristics of Make Time, which in combination distinguish this Chrysanthemum as a new and distinct cultivar.

1. Flat capitulum form;
2. Decorative capitulum type;
3. Lavender-rose ray floret color;
4. Exceptional number of flowers per break;
5. Diameter across capitulum face of 5.4 cm;
6. Spreading to upright branching pattern with an average of 5.4 breaks after a single pinch;
7. Flowering response approximately 63 days from the start of short days;
8. Relatively easy to control plant height such that the finished height ranges from 10 to 17 inches depending on pot size.

DESCRIPTION OF THE PHOTOGRAPH

Typical inflorescence and leaf characteristics of Make Time are illustrated in the accompanying color photograph showing a topview of the plant grown as a pinched spray pot mum in a 6.5" pot.

The plant was photographed using professional photographic techniques. The general lavender-rose tonality is best illustrated in top flowers on which light is directly focused. Flowers not directly under the light appear a deeper rose-lavender color.

DESCRIPTION OF THE PLANT

The following is a detailed description of the new Chrysanthemum plant's characeristics. The plant was vegetatively reproduced and grown in a greenhouse in Nipomo, Calif. for test purposes. Observations were made on plants grown as unrooted cuttings directly stuck into 6.5" pots under natural conditions of temperature and day length prevailing in Nipoma, Calif., during March-May, 1992.

Color designations are compared to the 1986 edition of R.H.S. Colour Chart, first published in 1966 by The Royal Horticultural Society, London, England. The B-NINE TM growth regulator referred to in the culturing procedures is 2,2-dimethyl hydrazide sold under the name of Daminozide or Alar and manufactured by Uniroyal.

THE PLANT

Origin: Progeny of cross between female parent Chrysanthemum Pink Arola (U.S. Plant Pat. No. 6,129) and male parent Chrysanthemum Cindy (U.S. Plant Pat. No. 6,838)

Classification:

*Botanic.*—*Dendranthema grandiflora.*

*Common name*—Chrysanthemum.

*Cultivar name.*—Make Time.

*Coding.*—14-AQ-AH-88 (England); CG90-0124 (United States).

INFLORESCENCE

Capitulum:

*Form.*—Shrub, flat.

*Type.*—Decorative.

*Diameter across face.*—5.4 cm (average).

Corolla of ray florets:

*Color.*—Lavender-rose (general tonality from distance of three meters). Front: R.H.S. 75A. Back: R.H.S. 75C.

*Shape.*—Elliptic.

Number of ray florets: 140.

Length of ray florets: 25 cm.

Width of ray florets: 1.12 cm.

Number of florets/break 8.4.

Disc floret color: Light green (immature), greenish-yellow (mature).

Reproductive Organs:

Androecium: Present disc and ray florets-very few-no pollen.

Gynoecium: Present disc and ray florets-very few.

GENERAL APPEARANCE

Height: Medium to short. When grown in a 6.5" pot with 1–4 applications of B-9, the plant height from the bottom of the pot may be maintained at 16–18 inches (9.5–12 inches plant height). When grown in a 4.5" pot with 1–4 height may be maintained at 10–12 inches (5.5–6.5 inches plant height).

Branching pattern: Upright and spreading with an average of 5.4 breaks when grown with one pinch as a spray pot.

Foliage:

*Color.*—Uniformly dark green. Upper Surface: R.H.S. 147A. Lower Surface: R.H.S. 147B.

*Mature leaf length.*—9.1 cm.

*Mature leaf width.*—5.9 cm.

*Shape.*—Typically 5-lobed with relatively deep indentations between lobes giving leaf a narrower appearance than other Chrysanthemums with comparable leaf length and width.

Growth habit: When grown in a 6.5" pot with 1–4 applications of B-9, the total plant height from the bottom of the pot may be maintained at 40–45 cm. When grown in a 4.5" pot with 1–4 applications of B-9, total plant height may be maintained at 25–30 cm.

Flowering response: Response is approximately 63 days from the start of short days.

Shelf life: Shelf life is typically 4 weeks, but often as long as 6 weeks, in contrast with some commercial varieties of Chrysanthemum with shelf life as low as 2 weeks.

What is claimed is:

1. A new and distinct Chrysanthemum cultivar, substantially as herein described and shown, characterized by lavender-rose ray floret color and a flat capitulum form with numerous flowers per break.

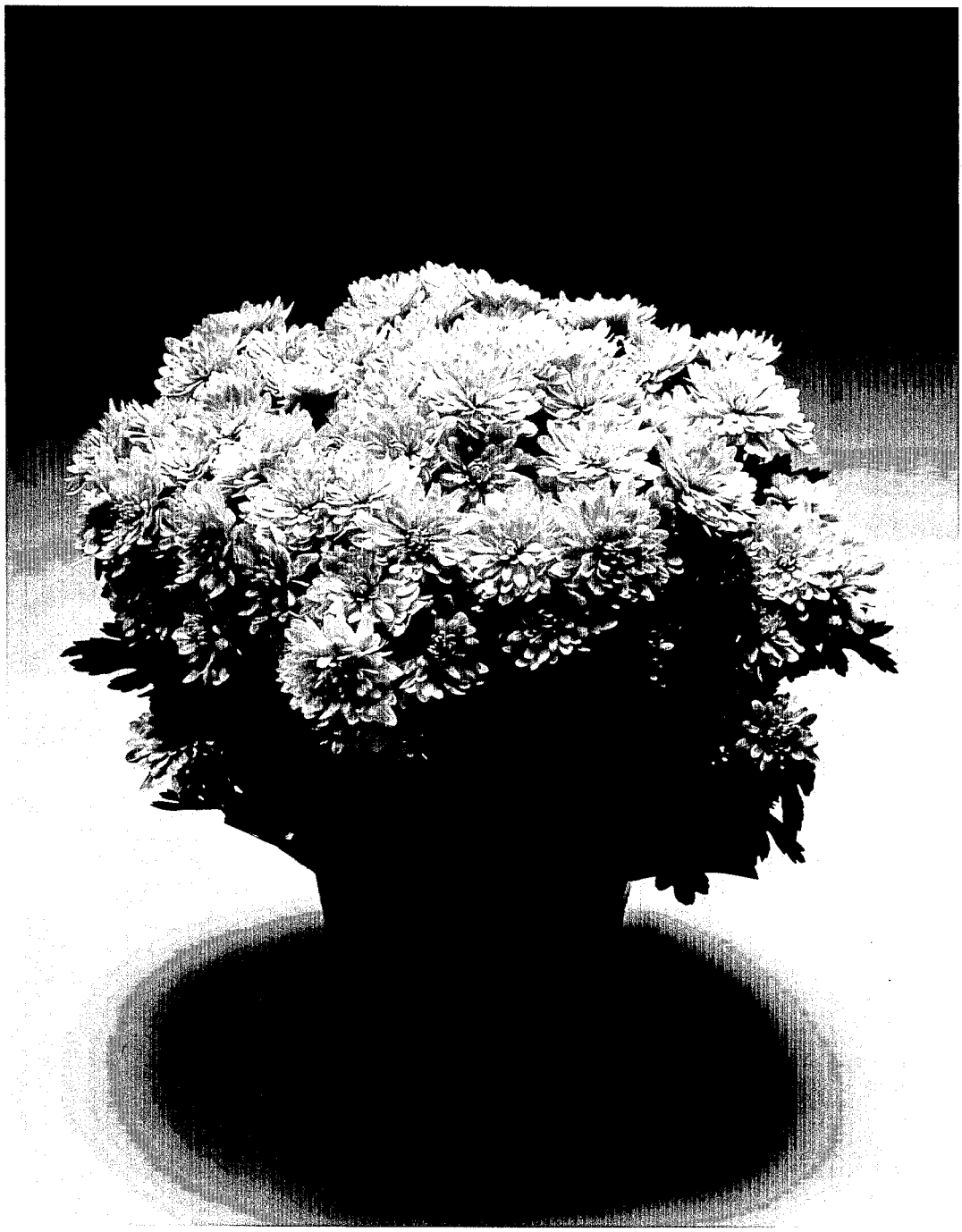

* * * * *